United States Patent
Spyrou et al.

(10) Patent No.: US 9,593,135 B2
(45) Date of Patent: Mar. 14, 2017

(54) COMPOSITIONS COMPRISING ALKOXYSILANE-CONTAINING ISOCYANATES AND ACID STABILISERS

(71) Applicants: Emmanouil Spyrou, Schermbeck (DE); Manfred Kreczinski, Herne (DE); Holger Loesch, Herne (DE); Andrea Thesing, Ahaus (DE); Lars Hellkuhl, Gescher (DE)

(72) Inventors: Emmanouil Spyrou, Schermbeck (DE); Manfred Kreczinski, Herne (DE); Holger Loesch, Herne (DE); Andrea Thesing, Ahaus (DE); Lars Hellkuhl, Gescher (DE)

(73) Assignee: EVONIK DEGUSSA GmbH, Essen (DE)

( * ) Notice: Subject to any disclaimer, the term of this patent is extended or adjusted under 35 U.S.C. 154(b) by 0 days.

(21) Appl. No.: 14/433,186

(22) PCT Filed: Sep. 25, 2013

(86) PCT No.: PCT/EP2013/069929
§ 371 (c)(1),
(2) Date: Apr. 2, 2015

(87) PCT Pub. No.: WO2014/063895
PCT Pub. Date: May 1, 2014

(65) Prior Publication Data
US 2015/0274760 A1   Oct. 1, 2015

(30) Foreign Application Priority Data

Oct. 23, 2012   (DE) .................. 10 2012 219 324

(51) Int. Cl.
| C08G 18/70 | (2006.01) |
| C07F 7/18 | (2006.01) |
| C08G 18/32 | (2006.01) |
| C08G 18/34 | (2006.01) |
| C08G 18/38 | (2006.01) |
| C08G 18/71 | (2006.01) |

(52) U.S. Cl.
CPC .......... *C07F 7/1836* (2013.01); *C07F 7/1892* (2013.01); *C08G 18/32* (2013.01); *C08G 18/34* (2013.01); *C08G 18/3819* (2013.01); *C08G 18/3876* (2013.01); *C08G 18/718* (2013.01)

(58) Field of Classification Search
None
See application file for complete search history.

(56) References Cited

U.S. PATENT DOCUMENTS

| 4,880,845 | A | * | 11/1989 | Moss | C08G 18/10 521/114 |
| 5,525,663 | A | * | 6/1996 | Oien | C08G 18/12 523/218 |
| 5,886,205 | A | * | 3/1999 | Uchida | C07F 7/1892 556/414 |
| 6,063,824 | A | * | 5/2000 | Krech | C08G 18/089 521/121 |
| 6,388,117 | B2 | * | 5/2002 | Pinske | C07F 7/1892 556/411 |
| 6,495,650 | B2 | | 12/2002 | Kohlstruk et al. | |
| 6,703,471 | B2 | | 3/2004 | Kohlstruk et al. | |
| 6,747,070 | B2 | | 6/2004 | Wenning et al. | |
| 6,825,240 | B2 | | 11/2004 | Wenning et al. | |
| 6,861,465 | B2 | | 3/2005 | Wenning et al. | |
| 6,914,115 | B2 | | 7/2005 | Spyrou et al. | |

(Continued)

FOREIGN PATENT DOCUMENTS

| EP | 1 010 704 | 6/2012 |
| WO | 2005 105879 | 11/2005 |

(Continued)

OTHER PUBLICATIONS

International Search Report Issued Jan. 20, 2014 in PCT/EP13/069929 filed Sep. 25, 2013.
Fujimoto, et al., "Crosslinkable silyl group-containing polyurethane/polyurea-based one-component solvent-free peelable pressure-sensitive adhesive for construction", XP002718271, 2006, (2 Pages) (Abstract only).
Furukawa, et al., "Self-curable silicone emulsion with good storage stability for tough coatings", XP002718272, 2000:267264, (2 Pages) (Abstract only).
Ono, Kazuhisa, "RTV silicone rubber compostions containing organotin compunds and isocyanatoalkyl-containing hydrolyzable silanes", XP002718273, 1999, (1 Page) (Abstract only).

*Primary Examiner* — Marc Zimmer
(74) *Attorney, Agent, or Firm* — Oblon, McClelland, Maier & Neustadt, L.L.P.

(57) ABSTRACT

The present invention relates to a composition comprising (A) an isocyanate of formula (I) $OCN-A-SiR^1R^2R^3$ (I), wherein A is straight-chain, branched, substituted and/or unsubstituted aliphatic hydrocarbyl of 1 to 12 carbon atoms or substituted or unsubstituted cycloaliphatic hydrocarbyl of 4 to 18 carbon atoms, wherein $R^1$ is selected from the group comprising $-O-R_{alk}$, wherein $R^2$ and $R^3$ are each independently selected from the group of substituents comprising $-R_{alk}$ and $-O-R_{alk}$, and wherein $-R_{alk}$ is hydrocarbyl of 1 to 6 carbon atoms, and B) a Bronstedt or Lewis acid or a compound which releases a Bronstedt or Lewis acid at room temperature; and also to a process for producing a stabilized alkoxysilane-containing isocyanate comprising the step of adding a Lewis or Bronstedt acid or a compound which releases a Bronstedt or Lewis acid at room temperature to an alkoxysilane-containing isocyanate.

12 Claims, No Drawings

(56) References Cited

U.S. PATENT DOCUMENTS

| | | |
|---|---|---|
| 6,924,385 B2 | 8/2005 | Lettmann et al. |
| 6,960,620 B2 | 11/2005 | Wenning et al. |
| 7,060,849 B1 * | 6/2006 | Childress .............. C07F 7/1892 556/414 |
| 7,307,135 B2 | 12/2007 | Spyrou |
| 8,222,312 B2 | 7/2012 | Spyrou et al. |
| 8,476,376 B2 | 7/2013 | Grenda et al. |
| 8,524,837 B2 | 9/2013 | Grenda et al. |
| 8,569,440 B2 | 10/2013 | Spyrou et al. |
| 8,674,050 B2 | 3/2014 | Spyrou |
| 8,702,899 B2 | 4/2014 | Spyrou et al. |
| 8,829,146 B2 | 9/2014 | Spyrou |
| 2002/0016486 A1 | 2/2002 | Pinske |
| 2004/0116639 A1 * | 6/2004 | Lim ....................... C09J 143/04 528/10 |
| 2005/0239956 A1 | 10/2005 | Spyrou et al. |
| 2005/0239992 A1 | 10/2005 | Spyrou et al. |
| 2007/0266897 A1 | 11/2007 | Spyrou |
| 2007/0282089 A1 | 12/2007 | Spyrou |
| 2008/0139753 A1 | 6/2008 | Spyrou et al. |
| 2008/0171816 A1 | 7/2008 | Spyrou et al. |
| 2008/0214728 A1 | 9/2008 | Spyrou et al. |
| 2008/0265201 A1 | 10/2008 | Spyrou et al. |
| 2008/0269415 A1 | 10/2008 | Spyrou et al. |
| 2010/0179273 A1 | 7/2010 | Spyrou et al. |
| 2010/0179282 A1 | 7/2010 | Spyrou et al. |
| 2010/0227942 A1 | 9/2010 | Spyrou et al. |
| 2011/0237740 A1 * | 9/2011 | Iyer ....................... C08G 18/10 524/590 |
| 2012/0071577 A1 | 3/2012 | Pfeffer et al. |
| 2012/0073472 A1 | 3/2012 | Spyrou et al. |
| 2012/0077932 A1 | 3/2012 | Pfeffer et al. |
| 2013/0041102 A1 | 2/2013 | Albrecht et al. |
| 2013/0041103 A1 | 2/2013 | Grenda et al. |
| 2013/0045652 A1 | 2/2013 | Schmidt et al. |
| 2013/0303042 A1 | 11/2013 | Schmidt et al. |
| 2014/0087613 A1 | 3/2014 | Spyrou et al. |
| 2014/0316056 A1 | 10/2014 | Grenda et al. |

FOREIGN PATENT DOCUMENTS

| | | |
|---|---|---|
| WO | 2005 105880 | 11/2005 |
| WO | 2008 028769 | 3/2008 |
| WO | 2008 068068 | 6/2008 |
| WO | 2008 068073 | 6/2008 |
| WO | 2008 138855 | 11/2008 |

* cited by examiner

COMPOSITIONS COMPRISING ALKOXYSILANE-CONTAINING ISOCYANATES AND ACID STABILISERS

The present invention relates to a composition comprising (A) an isocyanate of formula (I) OCN-A-SiR$^1$R$^2$R$^3$ (I), wherein A is straight-chain, branched, substituted and/or unsubstituted aliphatic hydrocarbyl of 1 to 12 carbon atoms or substituted or unsubstituted cycloaliphatic hydrocarbyl of 4 to 18 carbon atoms, wherein R$^1$ is selected from the group comprising —O—R$_{alk}$, wherein R$^2$ and R$^3$ are each independently selected from the group of substituents comprising —R$_{alk}$ and —O—R$_{alk}$, and wherein —R$_{alk}$ is hydrocarbyl of 1 to 6 carbon atoms, and B) a Bronstedt or Lewis acid or a compound which releases a Bronstedt or Lewis acid at room temperature; and also to a process for producing a stabilized alkoxysilane-containing isocyanate comprising the step of adding a Lewis or Bronstedt acid or a compound which releases a Bronstedt or Lewis acid at room temperature to an alkoxysilane-containing isocyanate.

Alkoxysilane-containing isocyanates are useful chemical compounds which facilitate the goal-directed construction of polymers which in the form of silane-containing polycarbamates or silane-containing polyureas, find diverse industrial use in foams, elastomers, thermoplastics, fibres, photostable polycarbamate coatings or adhesives.

The synthesis of isocyanates can take a number of different routes. The oldest and still predominant process for producing isocyanates on a large industrial scale involves phosgenation of the corresponding amines by use of phosgene, which is corrosive, highly toxic and contains a high proportion of chlorine and so is very costly and inconvenient to handle on an industrial scale. A series of unwanted chlorinated by-products are formed in this process in addition to the target products.

There are several processes which can be used to avoid the use of phosgene in the production of isocyanates on the industrial scale. The term "phosgene-free process" is frequently used in connection with the conversion of amines into isocyanates by use of alternative carbonylating agents, for example urea or dialkyl carbonate (EP 18 586, EP 355 443, U.S. Pat. No. 4,268,683, EP 990 644).

The so-called urea route is based on the urea-mediated conversion of amines into isocyanates via a two-step process. In the first step of the process, an amine is reacted with alcohol in the presence of urea or urea equivalents (e.g. alkyl carbonates, alkyl carbamates) to form a biscarbamate which is typically subjected to an intervening purification before being thermally cracked into isocyanate and alcohol in the second step of the process (EP 126 299, EP 126,300, EP 355 443, U.S. Pat. Nos. 4,713,476, 5,386,053). Alternatively, the actual process of carbamate formation can also be preceded by the separate production of a urea by deliberately reacting the amine with urea (EP 568 782). A two-step sequence comprising a partial reaction of urea with alcohol in the first and subsequent metered addition and carbamatization of the amine in the second step is also conceivable (EP 657 420).

The thermal cracking of carbamates can take place in the gas phase or in the liquid phase, with or without solvents and with or without catalysts. EP 126 299 and EP 126 300 describe processes for preparing hexamethylene diisocyanate and isophorone diisocyanate, respectively, by cracking the corresponding biscarbamates in the gas phase in a tubular reactor in the presence of metallic packing elements at 410° C.

The preparation of carbamates from an amine, urea and alcohol in a one-pot reaction with concurrent removal of ammonia is known from EP 18 568. The teaching of EP 18 568 was further developed and is described in EP 126 299, EP 126 300, EP 355 443, EP 566 925 and EP 568 782. Newer processes for preparing isocyanates are known from EP1512681, EP1512682, EP1512680, EP1593669, EP1602643, EP1634868, EP 2091911.

The reaction via the urea route, both in the synthesis of carbamates in one, two or else alternatively more steps and in the subsequent thermal cracking of the carbamates into isocyanates, leads to the formation of unwanted by-products, for example tertiary amines. It transpires that the by-products from the urea route affect the storage stability of the resultant alkoxy-silane-containing isocyanates to a considerable degree. In particular, the NCO content of the alkoxysilane-containing isocyanates shows a relative decline of up to 75% in the course of 4 weeks of storage at 50° C.

U.S. Pat. No. 7,060,849 B1 discloses the cracking of alkoxy-containing carbamates into alkoxy-containing isocyanates by neutralizing the catalyst with halogen-containing substances in order that unwanted trimerizates during the process may be avoided. However, there is nothing therein to suggest that these or other substances be added to the end product. Nor is the storage stability of the end product either tested or mentioned therein.

The problem addressed by the invention is that of using a phosgene-free process to provide novel compositions which avoid the abovementioned disadvantages and, more particularly, incur a relative NCO content loss of less than 25% in the course of four weeks of storage at 50° C.

The problem addressed by the present invention is further that of providing a process for phosgene-free preparation of stabilized compositions comprising alkoxysilane-containing isocyanates, especially to the effect that the loss of reactive NCO groups and/or the formation of disruptive by-products such as oligomers of the isocyanates is minimized.

The problem addressed by the invention is solved in a first aspect by a composition comprising A) an isocyanate of formula (I)

wherein A is straight-chain, branched, substituted and/or unsubstituted aliphatic hydrocarbyl of 1 to 12 carbon atoms or substituted or unsubstituted cycloaliphatic hydrocarbyl of 4 to 18 carbon atoms, wherein R$^1$ is selected from the group comprising —O—R$_{alk}$, wherein R$^2$ and R$^3$ are each independently selected from the group of substituents comprising —R$_{alk}$ and —O—R$_{alk}$, and wherein —R$_{alk}$ is hydrocarbyl of 1 to 6 carbon atoms, and B) a Bronstedt or Lewis acid or a compound which releases a Bronstedt or Lewis acid at room temperature.

In a first embodiment of the first aspect, the problem is solved by a composition wherein B) is selected from the group comprising carboxylic acids, preferably dicarboxylic acids, mineral acids, preferably phosphoric acid, acyl halides and alkyl or aryl halides.

In a second embodiment of the first aspect, which is also a mode of the first embodiment, the problem is solved by a composition wherein the Bronstedt or Lewis acid or the compound which releases a Bronstedt or Lewis acid at room temperature is a compound of formula (II)

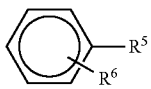
(II)

wherein R⁵ is selected from the group comprising halogen, —CO-halogen and —CH₂-halogen, and R⁶ is selected from the group comprising hydrogen, halogen, —CH₂-halogen and —CO-halogen, and preferably R⁵ is —CH₂—Cl or —CO—Cl and R⁶ is hydrogen.

In a third embodiment of the first aspect, which is also an embodiment of the first and second aspects, the problem is solved by a composition wherein the proportion of the Bronstedt or Lewis acid or of the compound which releases a Bronstedt or Lewis acid at room temperature is 0.0001 to 1 per cent, preferably 0.001 to 0.9 per cent and most preferably 0.002 to 0.5 per cent by weight of the mass of the isocyanate in the composition.

In a fourth embodiment of the first aspect, which is also an embodiment of the first to third aspects, the problem is solved by a composition wherein the isocyanate has the formula $OCN—(CH_2)_n—Si(OR^7)_3$ and n is 1 to 12, preferably 2 to 4 and $R^7$ is either methyl or ethyl.

In a fifth embodiment of the first aspect, which is also an embodiment of the first to fourth aspects, the problem is solved by a composition further comprising C) a compound having one or more, preferably two to four, NCO-reactive hydroxyl, thiol, —NH—, carbon-acid and/or amine groups.

In a sixth embodiment of the first aspect, which is also an embodiment of the first to fifth aspects, the problem is solved by a composition wherein the stoichiometric ratio between the totality of NCO-reactive hydroxyl, thiol, NH, carbon-acid and/or amine groups of C) to the totality of NCO groups of A) is 2:1 to 1:2, preferably 1.8:1 to 1:1.8 and most preferably 1.6:1 to 1:1.6.

In a second aspect, the problem addressed by the invention is solved by a process for preparing a polymer comprising the step of curing the composition according to the first aspect or an embodiment thereof.

In a first embodiment of the second aspect, the problem is solved by a process for preparing a stabilized alkoxysilane-containing isocyanate comprising the step of e) adding a Lewis or Bronstedt acid or a compound which releases a Bronstedt or Lewis acid at room temperature.

In a second embodiment of the second aspect, which is also a mode of the first embodiment, the problem is solved by a process further comprising the steps of a1) reacting an alkoxysilanealkylamine of formula (III)

with urea in the presence of an alcohol of formula $R^8$—OH to form a (cyclo)alkylenebisurea of formula (IV)

b1) reacting the (cyclo)alkylenebisurea of formula (IV) from step a) with an alcohol of formula $R^8$—OH to form a carbamate of formula (V)

or a2) reacting an alkoxysilanealkylamine of formula (III)

with urea in the presence of an alcohol of formula $R^8$—OH to form a carbamate of formula (V)

and also additionally to the combination of steps a1) and b1) or additionally to step a2)

c) removing the alcohol of formula $R^8$—OH after step b1) or a2) to form a reaction mixture separated from the alcohol, and d) thermally cracking the reaction mixture separated from the alcohol, at temperatures of 180 to 280° C. at a pressure of 0.1 to 200 mbar, wherein A is straight-chain, branched, substituted and/or unsubstituted aliphatic hydrocarbyl of 1 to 12 carbon atoms or substituted or unsubstituted cycloaliphatic hydrocarbyl of 4 to 18 carbon atoms, wherein $R^1$ is selected from the group comprising —O—$R_{alk}$, wherein $R^2$ and $R^3$ are each independently selected from the group of substituents comprising $R_{alk}$ and —O—$R_{alk}$, wherein $R_{alk}$ is hydrocarbyl of 1 to 6 carbon atoms, and wherein $R^8$ is substituted or unsubstituted alkyl, cycloalkyl, aryl or aralkyl.

In a third embodiment of the second aspect, which is also a mode of the first and second embodiments, the problem is solved by a process wherein the Bronstedt or Lewis acid or the compound which releases a Bronstedt or Lewis acid at room temperature is selected from the group comprising carboxylic acids, preferably dicarboxylic acids, mineral acids, acyl halides and alkyl or aryl halides.

In a fourth embodiment of the second aspect, which is also a mode of the first to third embodiments, the problem is solved by a process wherein the Bronstedt or Lewis acid or the compound which releases a Bronstedt or Lewis acid at room temperature is a compound of formula (II)

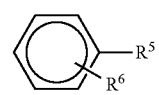
(II)

wherein R⁵ is selected from the group comprising halogen, —CO-halogen and —CH₂-halogen, and R⁶ is selected from the group comprising hydrogen, —CH₂-halogen, halogen and —CO-halogen, and preferably R⁵ is —CH₂—Cl or —CO—Cl and R⁶ is hydrogen.

In a fifth embodiment of the second aspect, which is also a mode of the first to fourth embodiments, the problem is solved by a process wherein the proportion of the Bronstedt or Lewis acid or of the compound which releases a Bronstedt or Lewis acid at room temperature is 0.0001 to 1 per cent, preferably 0.001 to 0.9 per cent and most preferably 0.002 to 0.5 per cent by weight of the sum of the acid and isocyanate.

In a sixth embodiment of the second aspect, which is also a mode of the first to fifth embodiments, the problem is solved by a process wherein the isocyanate has the formula $OCN—(CH_2)_n—Si(OMe)_3$ and n is from 1 to 12 and preferably from 2 to 4.

In a seventh embodiment of the second aspect, which is also a mode of the first to sixth embodiments, the problem is solved by a process wherein step b1) or step a) are carried out in a pressure distillation reactor with removal of resultant ammonia.

In a third aspect, the problem underlying the invention is solved by a use of a Bronstedt or Lewis acid or of a compound which releases a Bronstedt or Lewis acid at room temperature, for stabilizing an isocyanate of formula (I)

$$OCN-A-SiR^1R^2R^3 \qquad (I),$$

wherein A is straight-chain, branched, substituted and/or unsubstituted aliphatic hydrocarbyl of 1 to 12 carbon atoms or substituted or unsubstituted cycloaliphatic hydrocarbyl of 4 to 18 carbon atoms, wherein $R^1$ is selected from the group comprising —O—$R_{alk}$, wherein $R^2$ and $R^3$ are each independently selected from the group of substituents comprising —$R_{alk}$ and —O—$R_{alk}$, and wherein —$R_{alk}$ is hydrocarbyl of 1 to 6 carbon atoms, and wherein the composition further comprises a Bronstedt or Lewis acid or a compound which releases a Bronstedt or Lewis acid at room temperature.

In a first embodiment of the third aspect, the problem is solved by a use wherein the Bronstedt or Lewis acid or the compound which releases a Bronstedt or Lewis acid at room temperature is selected from the group comprising carboxylic acids, preferably dicarboxylic acids, mineral acids, acyl halides and alkyl or aryl halides.

In a second embodiment of the third aspect, which is also a mode of the first embodiment, the problem is solved by a use wherein the Bronstedt or Lewis acid or the compound which releases a Bronstedt or Lewis acid at room temperature is a compound of formula (II)

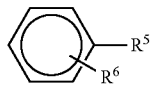

(II)

wherein $R^5$ is selected from the group comprising halogen, —CO-halogen and —$CH_2$-halogen, and $R^6$ is selected from the group comprising hydrogen, —$CH_2$-halogen, halogen and —CO-halogen, and preferably $R^5$ is —$CH_2$—Cl or —CO—Cl and $R^6$ is hydrogen.

In a third embodiment of the third aspect, which is also a mode of the first and second embodiments, the problem is solved by a use wherein the proportion of the Bronstedt or Lewis acid or of the compound which releases a Bronstedt or Lewis acid at room temperature is 0.0001 to 1 per cent, preferably 0.001 to 0.9 per cent and most preferably 0.002 to 0.5 per cent by weight of the sum of the acid and isocyanate.

In a fourth embodiment of the third aspect, which is also a mode of the first to third embodiments, the problem is solved by a use wherein the isocyanate has the formula OCN—$(CH_2)_n$—Si$(OR^7)_3$ and n is 1 to 12, preferably 2 to 4 and $R^7$ is either methyl or ethyl.

The inventors of the present invention found that acidic stabilizers surprisingly increase the storage stability of alkoxysilane-containing isocyanates obtained by a phosgene-free process in that the concentration of the reactive NCO groups of the isocyanates decreases distinctly more slowly in the presence of said stabilizers.

The inventors of the present invention have furthermore found that the formation of undesired by-products such as oligomers of the isocyanates is reduced in the presence of acidic stabilizers.

The invention relates to the stabilization of alkoxy-silane-containing isocyanates by acidic stabilizers which constitute component B) of the composition according to the present invention. According to the invention, component B) utilizes a Bronstedt or Lewis acid or chemical entities capable of releasing Bronstedt or Lewis acids at room temperature, examples being carboxylic acids, mineral acids or halogen-containing substances such as acyl halides or alkyl halides. Suitable compounds further include benzyl halides such as benzyl chloride or benzyl bromide, also benzoyl halides such as benzoyl chloride or benzoyl bromide, phthaloyl dichloride, isophthaloyl dichloride, terephthaloyl dichloride, toluoyl dichloride, oxalic acid, succinic acid or phosphoric acid. Benzyl chloride and benzoyl chloride are particularly preferred.

The preparation of isocyanates is extensively described in the prior art. Processes for continuous production of isocyanates by reaction of at least one amine with urea and/or urea equivalents and with at least one alcohol to form carbamates and subsequent thermal cracking of the carbamates into isocyanates are described in EP 18 568, EP 126 299, EP 126 300, EP 355 443, EP 566 925, for example. It is preferable to use processes as described in EP 1 512 681, EP 1 512 682, EP 1 512 680, EP 1 593 669, EP 1 602 643, EP 1 634 868, EP 2 091 911, EP 355 443, EP 568 782 and EP 2 091 911 for preparing isocyanates. A further precise description of individual process steps is more particularly derivable from WO 2008/077672-A pages 17 to 26. In a most preferable embodiment of the present invention, the alkoxysilane-containing isocyanate is prepared via a phosgene-free process.

According to the present invention, an acidic stabilizer or to be more precise a Lewis or Bronstedt acid or a compound which releases an acid of this type at room temperature can be added to the final alkoxy-silane-containing isocyanate. However, it is similarly possible to add the stabilizer during the preparation to a precursor of the alkoxysilane-containing isocyanate provided the stabilizer is not removed or deactivated by the subsequent steps of the synthesis. According to the present invention, a mixture comprising two or more stabilizers can be used as well as an individual stabilizer.

Starting compounds for the process are diamines of abovementioned formula (II), alcohols of abovementioned formula (III) and also urea and/or urea equivalents prepared from urea.

Suitable alkoxysilane-containing amines of formula (II) include, for example, aminopropyltrimethoxysilane, aminopropyltriethoxysilane, aminomethyltrimethoxysilane, aminomethyltriethoxysilane, aminopropyldimethoxymethylsilane, aminopropyldiethoxymethylsilane, aminomethyldimethoxymethylsilane, aminomethyldiethoxymethylsilane. Use of aminopropyltrimethoxysilane and aminopropyltriethoxysilane is preferred.

Suitable alcohols of formula $R^8$—OH are any desired primary and secondary aliphatic or cycloaliphatic alcohols having a boiling point below 190° C. under atmospheric pressure. In one preferred embodiment, $R^8$ is substituted or unsubstituted alkyl, cycloalkyl, aryl or aralkyl. C1-C6 alkanols such as methanol, ethanol, 1-propanol, 1-butanol, 2-butanol, 1-hexanol and cyclohexanol may be mentioned by way of example. Use of 1-butanol as alcohol is preferred.

Component A) may also contain additional di- and polyisocyanates. The di- and polyisocyanates used can consist of any desired aromatic, aliphatic and/or cycloaliphatic di- and/or polyisocyanates.

The compositions of the present invention can be in solid, viscous, liquid and also pulverulent form.

The compositions may additionally also contain auxiliary and additive materials selected from inhibitors, organic solvents, which optionally contain unsaturated groupings, surface-active substances, oxygen and/or free-radical traps, catalysts, light stabilizers, colour brighteners, photoinitiators, photosensitizers, thixotroping agents, anti-skinning agents, defoamers, dyes, pigments, fillers and delustrants. The amount varies greatly depending on field of use and type of auxiliary additive material.

Useful organic solvents include any liquid substances which do not react with other ingredients, examples being acetone, ethyl acetate, butyl acetate, xylene, Solvesso 100, Solvesso 150, methoxypropyl acetate and dibasic esters.

The usual additives, such as flow-control agents, e.g. polysilicones or acrylates, light stabilizers, e.g. sterically hindered amines, or other auxiliaries as described in EP 0 669 353 for example, can be added in an overall amount of 0.05 to 5 wt %. Fillers and pigments such as, for example, titanium dioxide can be added in an amount of up to 50 wt % of the overall composition.

The composition of the present invention is preferably obtained by mixing components A) and B) and optionally C).

The mixing of components A) and B) and optionally further components such as, for example, auxiliaries etc. can be carried out in suitable assemblies, stirred tanks, static mixers, tubular reactors, kneaders, extruders or other reaction-accommodating spaces with or without mixing function. The reaction is carried out at temperatures between room temperature and 220° C., preferably between room temperature and 120° C., and takes between a few seconds and several hours, depending on reaction components A) and B) and the temperature.

As far as applications are concerned, the composition of the present invention can be a main component, base component or added component of coatings (e.g. textile, paper and leather coatings), adhesives, varnishes, paints, powder coatings, printing inks, liquid inks, polishes, glazes, pigmentary pastes, masterbatches, spackling compounds, sealants, insulants, thermoplastic elastomers, especially thermoplastic polyurethanes, thermoset elastomers, foams (e.g. slabstock foams, moulded foams), semi-rigid foams (e.g. foam-backed films, energy-absorbing foams, fibre-reinforced foams), integral foams (e.g. rigid and flexible integral foams), thermoinsulants, RIM materials, materials for medical and hygiene applications (e.g. wound treatment), fibres, gels and microcapsules.

The composition of the present invention may further constitute a main component, base component or added component of RIM materials and UV resins of lenses and self-supporting film/sheet, thermoplastic polyurethanes (TPUs) for self-supporting film/sheet, hoses and powders, for example to manufacture moulded skins by the powder slush process, NCO-containing prepolymers for moisture-curing coatings and adhesives.

The composition of the present invention can further constitute a main component, base component or added component of coating compositions, especially primers, interlayers, topcoats, clearcoats, adhesives or sealing materials, preferably comprising compounds of component C) in particular.

The composition of the present invention may further constitute a main component, base component or added component of liquid and pulverulent lacquers coated on metal, plastics, glass, wood, textile, MDF (medium density fibre board) or leather substrates.

The composition of the present invention may further constitute a main component, base component or added component of adhesive compositions for adhesive bonding of metal, plastics, glass, wood, textile, paper, MDF (medium density fibre board) or leather substrates.

The composition of the present invention may further constitute a main component, base component or added component of metal-coating compositions, especially for automotive bodies, motorbikes, pushbikes, parts of buildings, domestic appliances, wood-coated compositions, glass-coated compositions, textile-coated compositions, leather-coated compositions and plastics-coated compositions.

The coating can either be used alone or be part of a layer of a multilayered build. It can be applied for example as a primer, as an interlayer or as a top- or clearcoat. The layers above or below the coating can be cured either thermally in the conventional manner or else by means of radiation.

The composition of the present invention in a preferred embodiment further comprises C) a compound having one or more, preferably two to four, NCO-reactive hydroxyl, thiol, —NH—, carbon-acid and/or amine groups. When C) is an alcohol, for example, the composition comprising A), B) and C) will cure to form a polyurethane compound.

Components A) and C) can be used in a mass ratio such that the OH:NCO ratio is between 2.0:1.0 and 1.0:2.0, preferably between 1.8:1.0 and 1.0:1.8 and more preferably between 1.6:1.0 and 1.0:1.6.

Polymers and prepolymers are obtainable in this way, preferably with an NCO number of 0-30% by weight and an OH number of 500-0 mg KOH/g and an acid number of 0-50 mg KOH/g) as well as thermoset or thermoplastic elastomers.

Any compounds having one or more, preferably two or more NCO-reactive functional groups are in principle suitable for use as compounds C). OH groups, $NH_2$ groups, NH groups, SH groups and carbon-acid groups are useful as functional groups, for example. Compounds C) preferably contain from 2 to 4 functional groups. Alcohol groups and/or amino groups are particularly preferred.

Suitable diamines and polyamines are: 1,2-ethylene-diamine, 1,2-propylenediamine, 1,3-propylenediamine, 1,2-butylenediamine, 1,3-butylenediamine, 1,4-butylenediamine, 2-(ethylamino)ethylamine, 3-(methylamino)-propylamine, 3-(cyclohexylamino)propylamine, 4,4'-diaminodicyclohexylmethane, isophoronediamine, 4,7-dioxadecane-1,10-diamine, N-(2-aminoethyl)-1,2-ethanediamine, N-(3-aminopropyl)-1,3-propanediamine, N,N"-1,2-ethanediylbis(1,3-propanediamine), adipic dihydrazide, diethylenetriamine, triethylenetetramine, tetraethylenepentamine, pentaethylenehexamine, dipropylenetriamine, hydrazine, 1,3-phenylenediamine, 1,4-phenylenediamine, 4,4'-diphenylmethanediamine, amino-functional polyethylene oxides and/or polypropylene oxides, adducts of salts of 2-acrylamido-2-methylpropane-1-sulphonic acid and hexamethylenediamines which may also bear one or more $C_1$-$C_4$ alkyl moieties. It is further also possible to use disecondary or primary/secondary diamines as obtainable for example in a known manner from the corresponding diprimary diamines by reaction with a carbonyl compound, for example a ketone or aldehyde, and subsequent hydrogenation or by addition of diprimary diamines onto acrylic esters or onto maleic acid derivatives.

Mixtures of the polyamines mentioned and further polyamines can also be used.

Examples of suitable amino alcohols are monoethanolamine, 3-amino-1-propanol, isopropanolamine, aminoethoxyethanol, N-(2-aminoethyl)ethanolamine, N-ethylethanolamine, N-butylethanolamine, diethanolamine, 3-(hydroxyethylamino)-1-propanol and diisopropanolamine and also mixtures thereof.

Suitable compounds C) having SH groups include, for example, trimethylolpropane tri-3-mercaptopropionate, pentaerythritol tetra-3-mercaptopropionate, trimethylolpropane trimermercaptoacetate and pentaerythritol tetramercaptoacetate.

Examples of suitable carbon-acid compounds are derivatives of malonic esters, acetylacetone and/or ethyl acetoacetate.

All dials and polyols having two or more OH groups and typically used in PU chemistry are suitable for use as compounds C).

Examples of dials and polyols used are ethylene glycol, 1,2-propanediol, 1,3-propanediol, diethylene glycol, dipropylene glycol, triethylene glycol, tetraethylene glycol, 1,2-butanediol, 1,4-butanediol, 1,3-butylethylpropanediol, 1,3-methylpropanediol, 1,5-pentanediol, bis(1,4-hydroxymethyl)cyclohexane (cyclohexanedimethanol), glycerol, hexanediol, neopentyl glycol, trimethylolethane, trimethylolpropane, pentaerythritol, bisphenol A, bisphenol B, bisphenol C, bisphenol F, norbornylene glycol, 1,4-benzyldimethanol, 1,4-benzyldiethanol, 2,4-dimethyl-2-ethylhexane-1,3-diol, 1,4-butylene glycol, 2,3-butylene glycol, di-β-hydroxyethylbutanediol, 1,5-pentanediol, 1,6-hexanediol, 1,8-octanediol, decanediol, dodecanediol, neopentyl glycol, cyclohexanediol, 3(4),8(9)-bis-(hydroxymethyl)tricyclo[5.2.1.0$^{2,6}$]decane (dicidol), 2,2-bis(4-hydroxycyclohexyl)propane, 2,2-bis[4-(β-hydroxyethoxy)phenyl]propane, 2-methyl-1,3-propanediol, 2-methyl-1,5-pentanediol, 2,2,4(2,4,4)-trimethyl-1,6-hexanediol, 1,2,6-hexanetriol, 1,2,4-butanetriol, tris(β-hydroxyethyl) isocyanurate, mannitol, sorbitol, polypropylene glycols, polybutylene glycols, xylylene glycol or neopentyl glycol hydroxypivalate, hydroxyacrylates, alone or mixed.

Particular preference is given to 1,4-butanediol, 1,2-propanediol, cyclohexanedimethanol, hexanediol, neopentyl glycol, decanediol, dodecanediol, trimethylolpropane, ethylene glycol, triethylene glycol, 1,5-pentanediol, 1,6-hexanediol, 3-methyl-1,5-pentanediol, neopentyl glycol, 2,2,4(2,4,4)-trimethylhexanediol and also neopentyl glycol hydroxypivalate. They are used alone or in mixtures.

Useful compounds C) further include diols and polyols which contain further functional groups. These are the well-known linear or slightly branched hydroxyl-containing polyesters, polycarbonates, polycaprolactones, polyethers, polythioethers, polyesteramides, polyacrylates, polyvinyl alcohols, polyurethanes or polyacetals. Their number-average molecular weight is preferably in the range from 134 to 20 000 g/mol and more preferably in the range from 134 to 4000 g/mol. Among the hydroxyl-containing polymers the preference is for using polyesters, polyethers, polyacrylates, polyurethanes, polyvinyl alcohols and/or polycarbonates having an OH number of 5-500 (in mg of KOH/gram).

Preference is given to linear or branched hydroxyl-containing polyols, more preferably polyester polyols, or mixtures of such polyesters. They are obtainable for example by reacting diols with deficient amounts of dicarboxylic acids, corresponding dicarboxylic anhydrides, corresponding dicarboxylic esters of lower alcohols, lactones or hydroxy carboxylic acids.

Diols and polyols suitable for preparing the preferred polyester polyols, in addition to the diols and polyols mentioned above, also include 2-methylpropanediol, 2,2-dimethylpropanediol, diethylene glycol, 1,12-dodecanediol, 1,4-cyclohexanedimethanol, 1,2-cyclohexanediol and 1,4-cyclohexanediol.

Preference is given to using 1,4-butanediol, 1,2-propanediol, cyclohexanedimethanol, hexanediol, neopentyl glycol, decanediol, dodecanediol, trimethylolpropane, ethylene glycol, triethylene glycol, 1,5-pentanediol, 1,6-hexanediol, 3-methyl-1,5-pentanediol, neopentyl glycol, 2,2,4(2,4,4)-trimethylhexanediol and also neopentyl glycol hydroxypivalate for preparing the polyester polyols.

Dicarboxylic acids or derivatives suitable for preparing the polyester polyols can be aliphatic, cycloaliphatic, aromatic and/or heteroaromatic in nature and can optionally be substituted, for example with halogen atoms, and/or be unsaturated.

The preferred dicarboxylic acids or derivatives include succinic acid, adipic acid, suberic acid, azelaic acid, sebacic acid, 2,2,4(2,4,4)-trimethyladipic acid, phthalic acid, phthalic anhydride, isophthalic acid, terephthalic acid, dimethyl terephthalate, tetrahydrophthalic acid, maleic acid, maleic anhydride and dimeric fatty acids.

Suitable polyester polyols also include polyester polyols obtainable in a known manner, via ring opening, from lactones, such as ε-caprolactone and simple diols as starter molecules. Similarly, mono- and polyesters of lactones, e.g. ε-caprolactone or hydroxy carboxylic acids, e.g. hydroxypivalic acid, ε-hydroxydecanoic acid, ε-hydroxycaproic acid, thioglycolic acid, can be used as starting materials for preparing polymers in the manner of the present invention. Polyesters formed from the polycarboxylic acids mentioned herein, or derivatives thereof, and polyphenols, such as hydroquinone, bisphenol A, 4,4'-dihydroxybiphenyl or bis(4-hydroxyphenyl) sulphone; polyesters of carbonic acid which are obtainable in a known manner from hydroquinone, diphenylolpropane, p-xylylene glycol, ethylene glycol, butanediol or 1,6-hexanediol and other polyols by customary condensation reactions, for example with phosgene or diethyl/diphenyl carbonate, or from cyclic carbonates, such as glycol carbonate or vinylidene carbonate, by polymerization; polyesters of silicic acid, polyesters of phosphoric acid, for example from methane-, ethane-, β-chlorethane-, benzene- or styrenephosphoric acid or derivatives thereof, e.g. phosphoryl chloride, phosphoric esters and polyalcohols or polyphenols of the abovementioned kind; polyesters of boric acid; polysiloxanes, for example the products obtainable by hydrolysis of dialkyldichlorosilanes with water and subsequent treatment with polyalcohols, those obtainable by addition of polysiloxane dihydrides onto olefins, such as allyl alcohol or acrylic acid, are useful as starting materials for preparing compounds C).

The polyesters are obtainable in a conventional manner by condensation in an inert gas atmosphere at temperatures of 100 to 260° C., preferably 130 to 220° C., in the melt or in azeotropic mode, as described for example in Methoden der Organischen Chemie (Houben-Weyl); volume 14/2, pages 1 to 5, 21 to 23, 40 to 44, Georg Thieme Verlag, Stuttgart, 1963, or in C. R. Martens, Alkyd Resins, pages 51 to 59, Reinhold Plastics Appl. Series, Reinhold Publishing Comp., New York, 1961.

It is likewise possible to use OH-containing (meth)acrylates and poly(meth)acrylates with preference. They are prepared by the co-polymerization of (meth)acrylates, wherein some components bear OH groups, others do not. This produces a random OH-containing polymer bearing no, one or many OH groups. Polymers of this type are described in High solids hydroxy acrylics with tightly controlled molecular weight. van Leeuwen, Ben. SC Johnson Polymer, Neth. PPCJ, Polymers Paint Colour Journal (1997), 187 (4392), 11-13; Special techniques for synthesis of high solid resins and applications in surface coatings. Chakrabarti, Suhas; Ray, Somnath. Berger Paints India Ltd., Howrah, India. Paintindia (2003), 53(1), 33-34, 36, 38-40; VOC protocols and high solid acrylic coatings. Chattopadhyay, Dipak K.; Narayan, Ramanuj; Raju, K. V.S.N. Organic Coatings and Polymers Division, Indian Institute of Chemical Technology, Hyderabad, India. Paintindia (2001), 51(10), 31-42.

The diols and dicarboxylic acids or derivatives thereof which are used to prepare the polyester polyols can be used in any desired mixtures. Mixtures of polyester polyols and diols can also be used.

Suitable compounds C) further include the reaction products of polycarboxylic acids and glycide compounds as described in DE-A 24 10 513 for example.

Examples of glycidyl compounds which can be used are esters of 2,3-epoxy-1-propanol with monobasic acids having 4 to 18 carbon atoms, such as glycidyl palmitate, glycidyl laurate and glycidyl stearate, alkylene oxides having 4 to 18 carbon atoms, such as butylene oxide, and glycidyl ethers, such as octyl glycidyl ether.

Compounds C) can also be compounds which in addition to an epoxy group additionally bear at least one further functional group, for example carboxyl, hydroxyl, mercapto or amino groups, which is capable of reacting with an isocyanate group. 2,3-Epoxy-1-propanol and epoxidized soybean oil are particularly preferred.

Any desired combinations of compounds C) can be used.

The present invention is further illustrated by the following figures and non-limiting examples whence further features, embodiments, aspects and advantages of the present invention are derivable.

EXAMPLES

Example 1

Preparation of Alkoxysilane-containing Isocyanates by the Urea Route

Preparation of isocyanatopropyltrimethoxysilane (IPMS) from aminopropyltrimethoxysilane (AMMO) and urea in the presence of methanol.

The uppermost tray of a pressure distillation reactor had applied to it an hourly feed of 360.2 g of AMMO, 127.9 g of urea melt and 386.2 g of methanol and the reaction mixture was boiled at 11-14 bar, 180° C. for an average residence time of 12.5 h with continuous removal of freed ammonia. The reactor effluent was freed of excess alcohol, low boilers and medium boilers in a flash container, together with the stream from the reurethanization stage, at 120° C. and 300 mbar and subsequent thin-film evaporation at 130° C. and 10 mbar. The crude IPMU thus obtained was subsequently separated in a short-path evaporator at 180° C. and a pressure of 0.1 mbar into a useful-product stream (IPMU) and a high-boiler stream.

407 g/h of IPMU were fed continuously into the circulation system of the falling film evaporator of the cracker and rectifier column, and the deblocking reaction was performed at a temperature of 195° C. and a pot pressure of 75 mbar in the presence of a steady-state concentration of tin dichloride at 50 ppm. The cracker gases IPMS and methanol were condensed out in two serially connected condensers at 85° C. and −25° C. The crude approximately 93% strength IPMS obtained was fed into a final distillation stage where 330 g/h of IPMS having a purity of >98.5% were obtained, which corresponds to a yield of 92%. 44 g/h of methanol were obtained as head product of the cracker and rectifier column. To maintain constant mass within the cracker and rectifier column and prevent deposits in and blockages of the cracker apparatus, a purge stream was continuously exported out of the circulation system and combined with 33.1 g/h of bottom product from the final IPMS distillation and the head product of the cracker and rectifier column, and the reurethanized stream was fed into the flash evaporation of the first step.

Example 2

Production of Storage-stable Compositions and Measurements of Storage Stability

The product of Example 1 (NCO content: 20.16 wt %) was stored at 50° C. for four weeks. Thereafter, the NCO content was 14.30 wt %. This corresponds to a relative NCO loss of 29%. When 0.1 wt % of benzoyl chloride was added to the product of Example 1, by contrast, the NCO content only dropped to 19.25 wt % in the course of the four weeks at 50° C. This corresponds to a relative NCO loss of 4.5%. When instead of the benzoyl chloride the same amount of succinic acid was used, the NCO content dropped to 18.34 wt % in the course of storage (relative loss, 9.0%). The stabilizer-containing compositions are thus significantly more stable in storage than the initial product.

The invention claimed is:

1. A composition comprising
A) an isocyanate of formula (I)

$$OCN-A-SiR^1R^2R^3 \qquad (I),$$

wherein A is a straight-chain, branched, substituted and/or unsubstituted aliphatic hydrocarbyl of 1 to 12 carbon atoms or substituted or unsubstituted cycloaliphatic hydrocarbyl of 4 to 18 carbon atoms, wherein $R^1$ has a formula —O—$R_{alk}$, wherein $R^2$ and $R^3$ are each independently selected from the group of substituents consisting of —$R_{alk}$ and —O—$R_{alk}$, and wherein —$R_{alk}$ is a hydrocarbyl of 1 to 6 carbon atoms, and B) a Bronstedt or Lewis acid or a compound which releases a Bronstedt or Lewis acid at room temperature selected from the group consisting of a carboxylic acid, a mineral acid, an acyl halide, an alkyl halide, an aryl halide and a mixture thereof wherein the Bronstedt or Lewis acid or the compound which releases a Bronstedt or Lewis acid at room temperature is present in an amount of 0.0001 to 1 per cent by weight of the mass of the isocyanate in the composition.

2. The composition according to claim 1, wherein the Bronstedt or Lewis acid or the compound which releases a Bronstedt or Lewis acid at room temperature is an aryl halide a compound of formula (II)

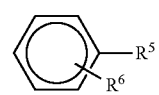

wherein $R^5$ is selected from the group consisting of halogen, —CO-halogen and —$CH_2$-halogen, and $R^6$ is selected from the group consisting of hydrogen, —CH$_2$-halogen, halogen and —CO-halogen.

3. The composition according to claim 1, wherein the isocyanate has a formula OCN—(CH$_2$)$_n$—Si(OR$^7$)$_3$ wherein n is 1 to 12 and R$^7$ is either methyl or ethyl.

4. The composition according to claim 1, further comprising
C) a compound having one or more NCO-reactive hydroxyl, thiol, —NH—, carbon-acid and/or amine groups.

5. The composition according to claim 4, wherein a stoichiometric ratio between a totality of NCO-reactive hydroxyl, thiol, NH, carbon-acid and/or amine groups of C) to a totality of NCO groups of A) is 2:1 to 1:2.

6. A process for preparing a polymer, comprising curing the composition according to claim 4.

7. A process for preparing a stabilized alkoxysilane-containing isocyanate, comprising
e) adding a Lewis or Bronstedt acid or a compound which releases a Bronstedt or Lewis acid at room temperature to an alkoxysilane-containing isocyanate,
wherein the Bronstedt or Lewis acid or the compound which releases a Bronstedt or Lewis acid at room temperature is present in an amount of 0.0001 to 1 per cent by weight of the sum of the acid and isocyanate.

8. A process for preparing a stabilized alkoxysilane-containing isocyanate, comprising
a1) reacting an alkoxysilanealkylamine of formula (III)

H$_2$N-A-SiR$^1$R$^2$R$^3$ (III)

with urea to form a (cyclo) alkylenebisurea of formula (IV)

H$_2$N—OC—NH-A-SiR$^1$R$^2$R$^3$ (IV), b1) reacting the (cyclo)alkylenebisurea of formula (IV) from a) with an alcohol of formula R$^8$—OH to form a carbamate of formula (V)

R$^8$O—OC—NH-A-SiR$^1$R$^2$R$^3$ (V)

or
a2) reacting an alkoxysilanealkylamine of formula (III)

H$_2$N-A-SiR$^1$R$^2$R$^3$ (III)

with urea in the presence of an alcohol of formula R$^8$—OH to form a carbamate of formula (V)

R$^8$O—OC—NH-A-SiR$^1$R$^2$R$^3$ (V), and also additionally to the combination of a1) and b1) or additionally to a2)
c) removing the alcohol of formula R$^8$—OH after b1) or a2) to form a reaction mixture separated from the alcohol, and d) thermally cracking the reaction mixture separated from the alcohol, at a temperature of 180 to 280° C. at a pressure of 0.1 to 200 mbar,
wherein A is a straight-chain, branched, substituted and/or unsubstituted aliphatic hydrocarbyl of 1 to 12 carbon atoms or substituted or unsubstituted cycloaliphatic hydrocarbyl of 4 to 18 carbon atoms,
wherein R$^1$ has a formula —O—R$_{alk}$,
wherein R$^2$ and R$^3$ are each independently selected from the group of substituents consisting of —R$_{alk}$ and —O—R$_{alk}$,
wherein —R$_{alk}$ is hydrocarbyl of 1 to 6 carbon atoms, and
wherein R$^8$ is a substituted or unsubstituted alkyl, cycloalkyl, aryl or aralkyl; and
e) adding a Lewis or Bronstedt acid or a compound which releases a Bronstedt or Lewis acid at room temperature to an alkoxysilane-containing isocyanate.

9. The process according to claim 7, wherein the Bronstedt or Lewis acid or the compound which releases a Bronstedt or Lewis acid at room temperature is selected from the group consisting of a carboxylic acid, a mineral acid, an acyl halide, an alkyl halide, and an aryl halide.

10. The process according to claim 7, wherein the isocyanate has a formula OCN—(CH$_2$)$_n$—Si(OMe)$_3$ wherein n is from 1 to 12.

11. The process according to claim 8, wherein b1) or a) are carried out in a pressure distillation reactor with removal of resultant ammonia.

12. A composition consisting essentially of
A) an isocyanate of formula (I)

OCN-A-SiR$^1$R$^2$R$^3$ (I), wherein A is a straight-chain, branched, substituted and/or unsubstituted aliphatic hydrocarbyl of 1 in 12 carbon atoms or substituted or unsubstituted cycloaliphatic hydrocarbyl of 4 to 18 carbon atoms,
wherein R$^1$ has a formula —O—R$_{alk}$,
wherein R$^2$ and R$^3$ are each independently selected from the group of substituents consisting of —R$_{alk}$ and —O—R$_{alk}$, and
wherein —R$_{alk}$ is a hydrocarbyl of 1 to 6 carbon atoms, and
B) a Bronstedt or Lewis acid or a compound which releases a Bronstedt or Lewis acid at room temperature which is selected from the group consisting of a carboxylic acid, a mineral acid, an acyl halide, an alkyl halide, an aryl halide and a mixture thereof.

* * * * *